United States Patent
Brown et al.

[19]

[11] Patent Number: 6,110,148
[45] Date of Patent: *Aug. 29, 2000

[54] CAPACITANCE-BASED DOSE MEASUREMENTS IN SYRINGES

[75] Inventors: Stephen J. Brown, Mountain View; David R.L. Worthington, La Honda, both of Calif.

[73] Assignee: Health Hero Network, Inc., Mountain View, Calif.

[*] Notice: This patent is subject to a terminal disclaimer.

[21] Appl. No.: 08/972,670

[22] Filed: Nov. 18, 1997

Related U.S. Application Data

[63] Continuation-in-part of application No. 08/681,314, Jul. 22, 1996, Pat. No. 5,720,733, which is a continuation-in-part of application No. 08/278,929, Jul. 22, 1994, Pat. No. 5,569,212.

[51] Int. Cl.[7] ........................................... A61M 5/00
[52] U.S. Cl. ............................ 604/207; 604/246; 222/23; 222/30
[58] Field of Search ........................... 604/207–211, 246, 604/65–67; 235/451; 222/23, 30; 128/DIG. 1; 73/861.08

[56] References Cited

U.S. PATENT DOCUMENTS

| | | | |
|---|---|---|---|
| 4,853,521 | 8/1989 | Claeys et al. | 235/375 |
| 4,950,246 | 8/1990 | Muller | 604/154 |
| 5,019,974 | 5/1991 | Beckers | 364/413.02 |
| 5,176,502 | 1/1993 | Sanderson et al. | 417/18 |
| 5,569,212 | 10/1996 | Brown . | |
| 5,704,922 | 1/1998 | Brown . | |
| 5,720,733 | 2/1998 | Brown . | |
| 5,882,338 | 3/1999 | Gray . | |

*Primary Examiner*—Mark Bockelman
*Attorney, Agent, or Firm*—Black Lowe & Graham PLLC

[57] ABSTRACT

Measurements of insulin quantities in a syringe are performed capacitively in an integrated insulin dose recorder/blood glucose meter. The syringe is placed in a holder before and after the administration of the dose. Capacitor electrodes may be situated within the syringe and/or outside the syringe in various geometries. Liquid quantities in the syringe are determined by comparing capacitive response patterns of the syringe with calibration data stored in the device. Dose histories are downloaded to a patient computer for transfer to a clinician's computer. Standard or customized syringes may be used.

24 Claims, 4 Drawing Sheets

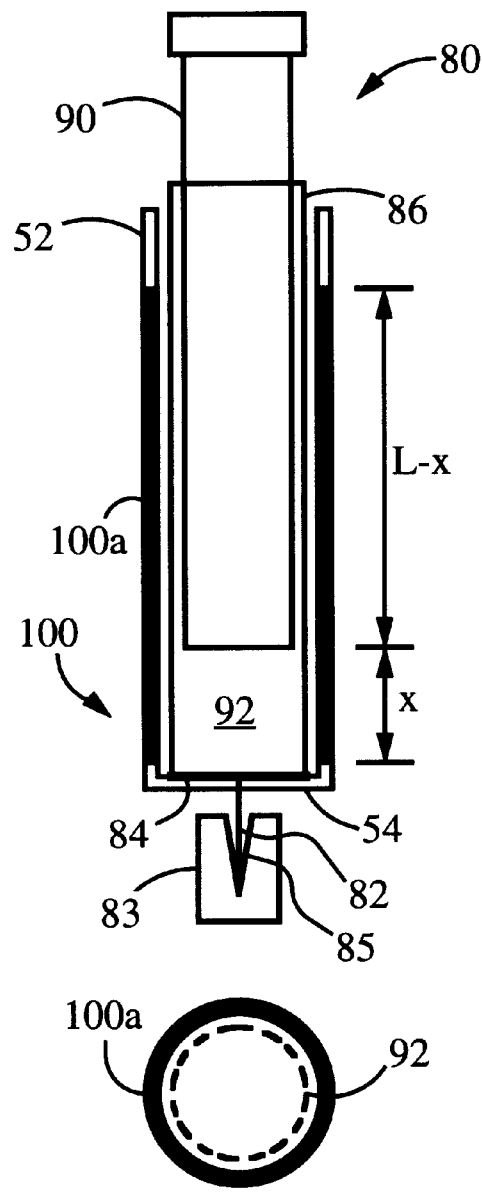
FIG. 3-A
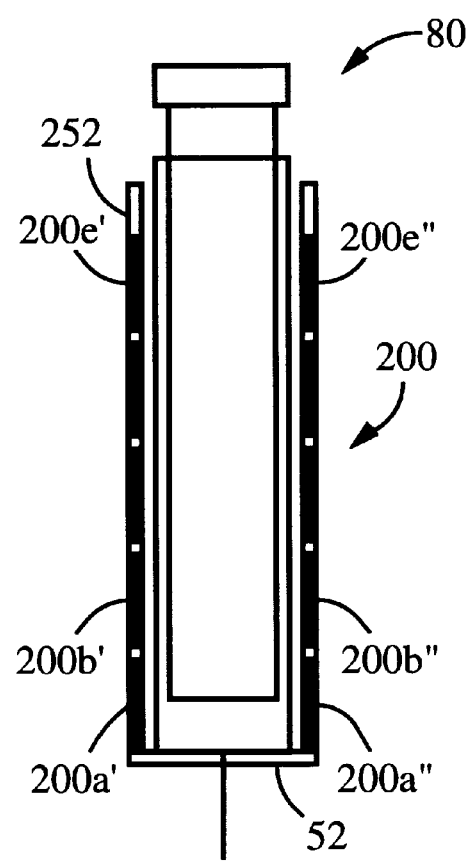
FIG. 4-A
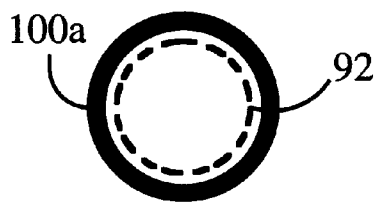
FIG. 3-B
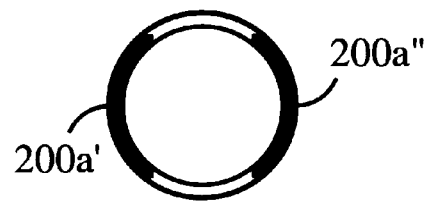
FIG. 4-B

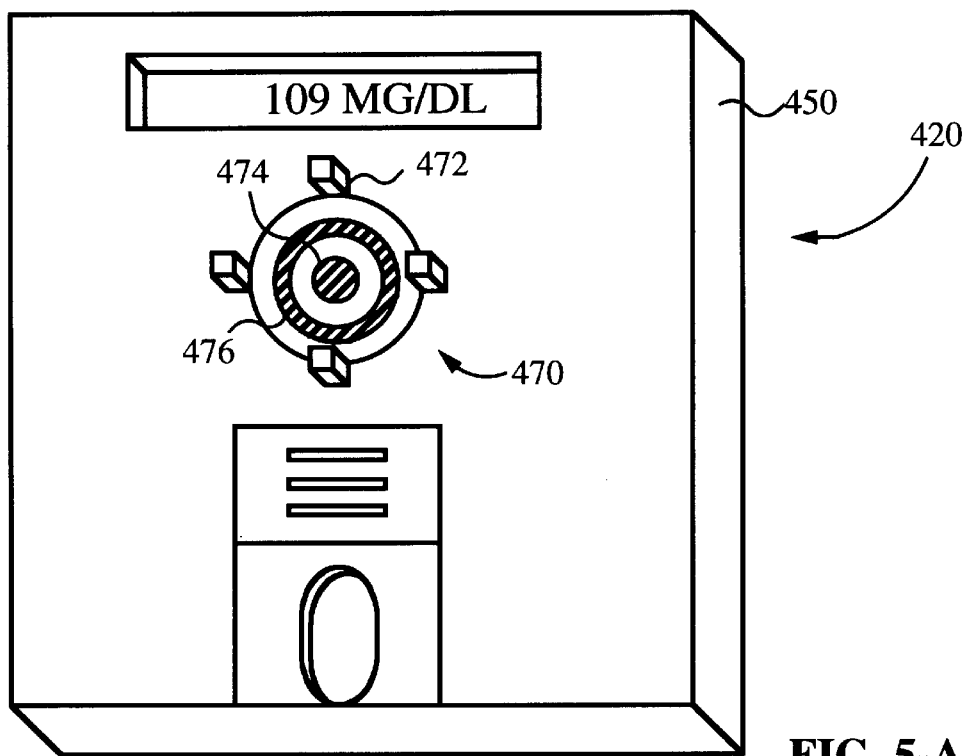
FIG. 5-A
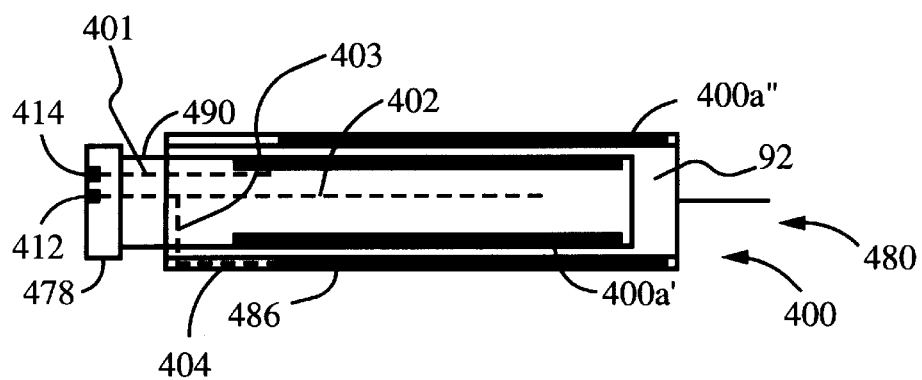
FIG. 5-B

CAPACITANCE-BASED DOSE MEASUREMENTS IN SYRINGES

RELATED APPLICATION DATA

This application is a continuation-in-part of U.S. patent application Ser. No. 08/681,314 entitled "Apparatus for Determining and Recording Injection Doses in Syringes Using Electrical Capacitance Measurements" filed on Jul. 22, 1996 now U.S. Pat. No. 5,720,733 which is a continuation-in-part of U.S. patent application Ser. No. 08/278,929 filed on Jul. 22, 1994 (now U.S. Pat. No. 5,569,212) and is related to U.S. patent application Ser. No. 08/591,308 (now U.S. Pat. No. 5,628,309). This application is related to U.S. patent application Ser. No. 08/681,290 filed Jul. 22, 1996, now U.S. Pat. No. 5,782,814, Ser. No. 08/681,223 filed Jul. 22, 1996 now U.S. Pat. No. 5,792,117, and 08/898,711, filed Jul. 22, 1997, now abandoned, as well as to the co-filed application Ser. No. 08/972,375 filed Nov. 18, 1997 entitled "Inductance-Based Dose Measurements in Syringes" by inventors Stephen J. Brown and Erik K. Jensen now pending. All of the above applications are assigned to the assignee of the present invention, and are herein incorporated by reference.

FIELD OF THE INVENTION

This invention relates to injection syringes and patient monitoring devices, and in particular to an apparatus for electronically recording capacitance-based measurements of doses of an agent delivered with an injection syringe.

BACKGROUND OF THE INVENTION

In recent years, the value of keeping electronic medical records in place of paper records has been widely recognized in the health care industry. The use of electronic medical records allows health care providers and patients to store, retrieve, and share medical information with considerably more ease and accuracy. The sharing of medical information is particularly important in treatment programs involving the injection of insulin, human growth hormone, or other medications.

Typically, these injections are performed using disposable syringes. Unfortunately, no adequate apparatus exists that measures and electronically records dose information from a disposable syringe. As a result, the patient or health care worker performing the injection is burdened with the task of injecting the dose and then manually recording the dose amount in a log book.

Because of the frequency of such injections, often several times a day for diabetics, it becomes difficult for a patient to keep accurate records. Indeed, studies have shown that a patient's own records and recollections are often incomplete and inaccurate. Additionally, a patient may intentionally cheat while making self-recorded entries in an attempt to create a log book that will please his or her doctor. In the long-term this makes patient monitoring extremely difficult and jeopardizes the treatment program, possibly even endangering the patient's life.

Attempts have been made at developing electronic management systems for assisting patients in self-administered drug programs. For example, U.S. Pat. No. 5,019,974 issued to Beckers describes a hand-held, microprocessor-based recorder that interfaces with a master computer. The patient enters therapy information into the recorder via a keyboard. The recorder includes a display for displaying treatment therapy guidelines to the patient. The recorder also has a blood glucose meter for recording the patient's blood glucose levels.

The recorder described by Beckers does not automatically measure and record dose information from a disposable syringe. After injecting a dose, the patient must manually enter the dose information into the recorder using switches or keys. Although this is an improvement over keeping written records on paper, the effectiveness of the drug program is still limited by the patient's recollections and recordings, which are unreliable.

Attempts have also been made at developing devices that deliver a predetermined dose of medication and record the dose amount. For example, U.S. Pat. No. 5,176,502 issued to Sanderson et al. on Jan. 5, 1993 describes a syringe pump for expelling a preset dose of medication from a syringe. The syringe pump includes a syringe retainer for holding the syringe and a driver for engaging the plunger of the syringe. An electric motor pushes the driver and plunger into the syringe barrel to expel the medication.

The syringe pump further includes a monitoring circuit for monitoring the motion of the driver during the delivery of the medication. The monitoring circuit includes a linear potentiometer having an electrically conductive strip of resistive material. The resistive material is positioned such that it engages an electrical contact of the driver. The position of the electrical contact on the resistive strip varies the voltage of the monitoring circuit, thus indicating the position of the plunger inside the barrel. A microprocessor receives voltage signals from the monitoring circuit and compares the voltage signals to preprogrammed signals to determine if the plunger displacement corresponds to correct displacement for delivering the preset dose. A control mechanism connected to the microprocessor regulates the driver's movement to ensure the preset dose of medication is delivered.

Although the syringe pump described by Sanderson does allow electronic recording of dose information, it is only designed to deliver medication directly into an intravenous line. It is not designed to inject a patient directly nor can it measure and record a dose from a syringe unless the syringe pump pushes the plunger. Consequently, the syringe pump is of little use to a health care worker who must inject a patient directly, or to an outpatient who must follow a self-injection treatment program.

Another device for injecting a preset dose of medication and for recording the injected dose is disclosed in U.S. Pat. No. 4,950,246 issued to Muller on Aug. 21, 1990. Muller describes a battery-operated injection pen having a pump rod driven by an electric motor. The electric motor is controlled by an electronic control unit that includes a microprocessor with a memory for storing dose information. The injection pen further includes a sensor connected to the control unit for electrically determining the position of the pump rod, and thus the amount of medication injected.

Although the injection pen described by Muller measures and electronically records dose information, it has several disadvantages that have precluded its widespread use. The injection pen is an expensive device requiring complicated electronic equipment to deliver and record doses. Moreover, because the injection pen integrates a syringe and electronic recorder into one device, it is not disposable. The patient must use it repeatedly for each injection, even after the injection pen has been contaminated with blood. Consequently, the injection pen does not provide an inexpensive, convenient, or hygienic solution to patients wishing to measure and electronically record injected dose information.

U.S. Pat. No. 4,853,521 issued to Ronald Claeys on Aug. 1, 1989 presents a programmable, intelligent reader unit which receives and records drug data using hand-held or fixed scanners. The scanners read bar codes in place on syringes, ampules, flow meters, etc. In addition, this intelligent reader allows the user to weigh a syringe before and after injection to determine and record the administered amount of medicine. Dosage data logged in this manner can be displayed or printed out in the form of a record.

Operating the device described by Ronald Claeys requires many complicated steps of weighing syringes, scanning in bar codes, etc. The complexity of the required procedures as well as the high cost of the apparatus have precluded its widespread use. Additionally, the device cannot be easily carried by the user for recording doses while away from the health care facility or home. Thus, no inexpensive apparatus exists for determining and electronically recording dose information from a disposable syringe. Further, no such apparatus exists that is both simple in operation and easily carried by a user.

OBJECTS AND ADVANTAGES OF THE INVENTION

It is a primary object of the present invention to provide an apparatus for capacitively determining and electronically recording an injection dose delivered from a disposable syringe. It is another object of the invention to provide an apparatus that may be easily operated and carried by a user. A further object of the invention is to suit the apparatus to diabetic patients, and to diabetes home care in particular. It is yet another object to provide an apparatus facilitating automated paperless data processing, from the measurement performed by the patient to the recording at the clinic. These and other objects and advantages will become more apparent after consideration of the ensuing description and drawings.

SUMMARY OF THE INVENTION

An apparatus for capacitively measuring and electronically recording a dose delivered using a syringe comprises: a holder for receiving and holding a syringe in a measurement position; a capacitive element coupled to the holder and enclosing the syringe such that a capacitive response of the capacitive element is indicative of the dose when the syringe is in the measurement position; a measuring device connected to the capacitive element for measuring capacitive responses of the capacitive element; and a recording device connected to the measuring device for recording a dose datum indicative of the capacitive response and thus indicative of the dose.

Preferably, the holder comprises a well laterally enclosing the syringe when the syringe is in the measurement position. The capacitive element is then coupled to the well such that at least one electrode of the capacitive element laterally encloses the syringe when the syringe is in the measurement position. In one embodiment, the capacitive element is defined between the liquid held in the syringe and an external electrode situated outside the syringe. A needle contact coupled to the holder is then used to establish electrical communication between the measuring device and the liquid, through the syringe needle, when the syringe is in the measurement position. In another embodiment, the capacitive element is defined between first and second electrically conducting longitudinal plates coupled to the holder, electrically insulated from each other, and situated opposite each other relative to the syringe.

In yet another embodiment, the capacitive element is situated entirely within the syringe. Two coaxial cylindrical electrodes, one near the inside surface of the syringe barrel and the other near the outside surface of the syringe plunger, are connected to input and output terminals on the outside of the syringe barrel. The housing comprises a contact field coupled to the outside of the housing. The contact field comprises an input contact for contacting the input terminal, and an output contact for contacting the output terminal. The input and output contacts are connected to the measuring device.

A port connected to the recording device is used to download data stored in the recording device to an external storage or communication device such as a host computer. Also connected to the recording device is a testing device for testing a physical condition of the patient and generating condition data representative of the physical condition. The recording device records the condition data. Preferably, the testing device is a blood glucose meter and the physical condition is the patient's blood glucose level. A display connected to the measuring device is used to display recorded doses and blood glucose levels to the patient. A computing device is connected to the recording device. The computing device computes dose data from measured capacitive responses and stored calibration data, for storage in the recording device. Dose data preferably comprises administered doses. The calibration data, stored in a calibration memory device, is indicative of the correspondence between capacitive responses and dose data for the particular syringe used by the patient. The calibration data generated by measuring capacitive responses for the entire range of potential liquid quantities in the syringe, and recording the correspondence between liquid quantities and capacitive responses.

A housing encloses the measuring and recording devices, and preferably encloses and magnetically shields the capacitive element. The holder is mechanically coupled to the housing. The housing is sufficiently compact to be hand-held and carried by a user. The capacitive element preferably consists of a single capacitor, and the capacitive response preferably comprises the capacitance of the capacitor. In an alternative embodiment, the capacitive element comprises plural longitudinally-spaced capacitors, and the capacitive response comprises an capacitive response pattern.

DESCRIPTION OF THE FIGURES

FIG. 3-A shows a longitudinal sectional view of a syringe situated in a measurement position within a holder encapsulating one electrode of a capacitive element, according to a preferred embodiment of the present invention.

FIG. 3-B shows a transverse sectional view of the holder and syringe of FIG. 3-A.

FIG. 4-A shows a longitudinal sectional view of a syringe, holder, and capacitor arrangement according to an alternative embodiment of the present invention.

FIG. 4-B shows a transverse sectional view of the holder and syringe of FIG. 4-A.

FIG. 5-A shows a perspective view of an apparatus suitable for use with a syringe comprising an internal capacitor, according to an alternative embodiment of the present invention.

FIG. 5-B shows a longitudinal sectional view of a syringe capacitor geometry suitable for use with the apparatus of FIG. 5-A.

DETAILED DESCRIPTION

Figure 1:
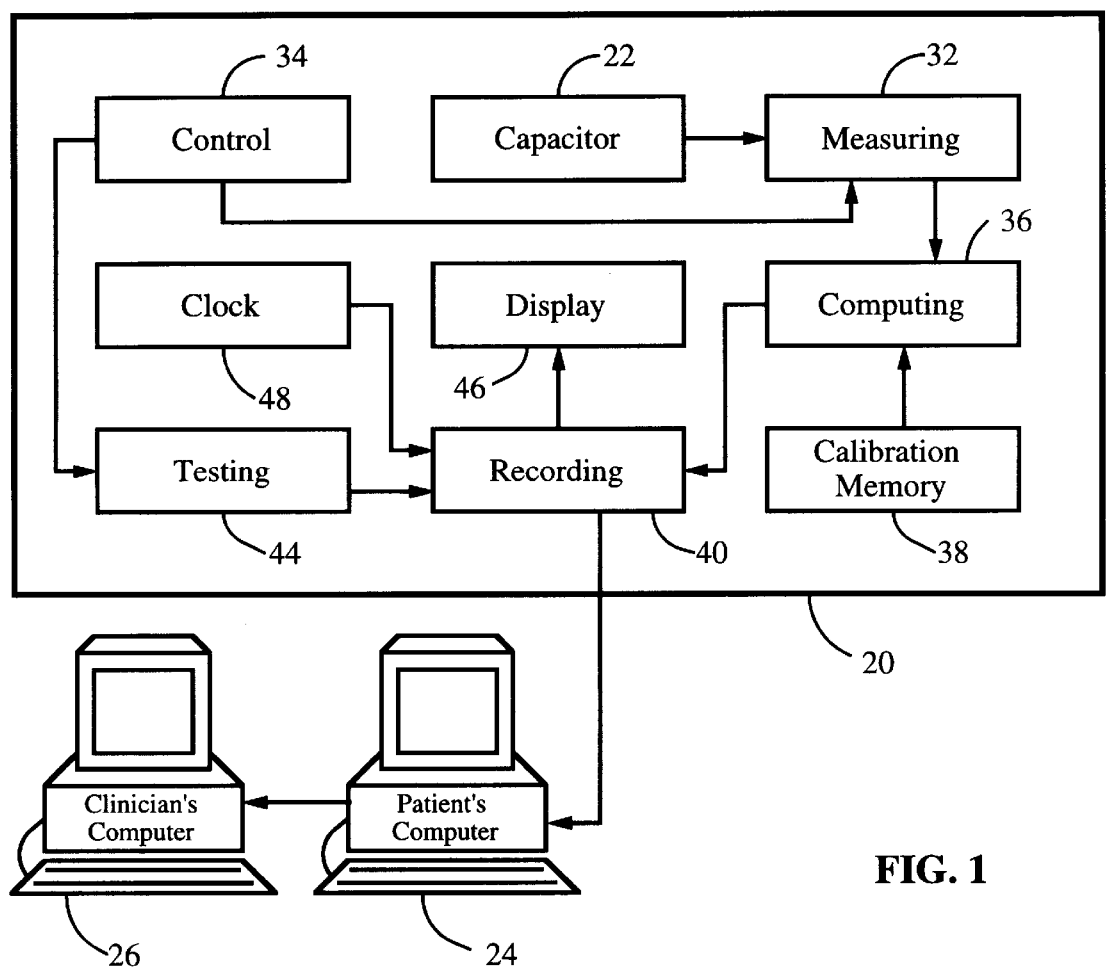
FIG. 1 is a high-level schematic diagram illustrating the structure of a preferred apparatus of the present invention.

FIG. 1-A is a high-level schematic diagram illustrating a preferred apparatus 20 of the present invention. Apparatus 20 records data indicative of doses delivered to a patient using a syringe. Apparatus 20 is capable of downloading the recorded data to a patient computer 24, which in turn is capable of communicating with a clinician's computer 26 over a long-distance communication line such as a telephone line or the Internet.

Apparatus 20 comprises a capacitive element 22 enclosing at least part of the syringe. Capacitive element 22 comprises one or more capacitors arranged in a predetermined spatial relationship. A measuring device 32 is in electrical communication with capacitive element 22, and detects a capacitive response of capacitive element 22 when the syringe is in a predetermined measurement position. Measuring device 32 preferably comprises a LC circuit with a resonant frequency $\omega = 1/\sqrt{LC}$. Capacitance-measuring devices are well known in the art. The capacitive response of capacitive element 22 is indicative of the quantity of liquid in the syringe, and consequently of the dose administered to the patient using the syringe. A control device 34 is in electrical communication with measuring device 32, and temporally controls the operation of measuring device 32. Control device 34 is capable of turning-on measuring device 32 when the syringe is in the measurement position, for example before the administration of the dose to the patient. Control device 34 preferably comprises a button which the patient can press to trigger a measurement.

A computing device 36 is in electrical communication with measuring device 32 and with a calibration memory 38. Computing device 36 preferably comprises a microprocessor. Computing device 38 is further in electrical communication with a recording device 40. Recording device 40 preferably comprises a memory chip. Computing device 36 generates dose data to be stored in recording device 40. The dose data preferably comprises a dose (e.g. insulin dose) administered to the patient, but may be in general any data which can be used to reconstruct (for example within apparatus 20, at patient computer 24, or at clinician computer 26) the dose administered to the patient. In particular, computing device 36 calculates the quantity of liquid within the syringe before injection of a dose, or the difference between the liquid quantities within the syringe before and after injection. Computing device 36 then sends the result (the dose) to recording device 40 for storage.

Computing device 36 determines liquid quantities by comparing capacitive response data received from measuring device 32 with predetermined calibration data stored in calibration memory 38. The calibration data is indicative of the correspondence between capacitive responses and liquid quantities for the entire range of potential liquid quantities in the syringe. That is, calibration memory 38 stores the liquid quantity corresponding to a given capacitive response of capacitive element 22, for all liquid quantities potentially present in the syringe.

A testing device 44 is electrically connected to recording device 40. Testing device 44 tests a physical condition of the patient, and generates condition data representative of the physical condition. Preferably, the physical condition is diabetes, the testing device comprises a conventional blood glucose meter, and the condition data comprises a blood glucose level of the patient. Recording device 40 records the condition data generated by testing device 44. A display 46 is electrically connected to recording device 40, and displays dose data and condition data to the patient. Display 46 is preferably a conventional liquid crystal display (LCD). A display such as display 46 may be in general directly connected to computing device 36 and testing device 44, rather than indirectly through recording device 40. A digital clock 48 is connected to recording device 40. Upon prompting, clock 48 sends the current date and time to recording device 40 for recording in conjunction with dose or condition data.

Figure 2:
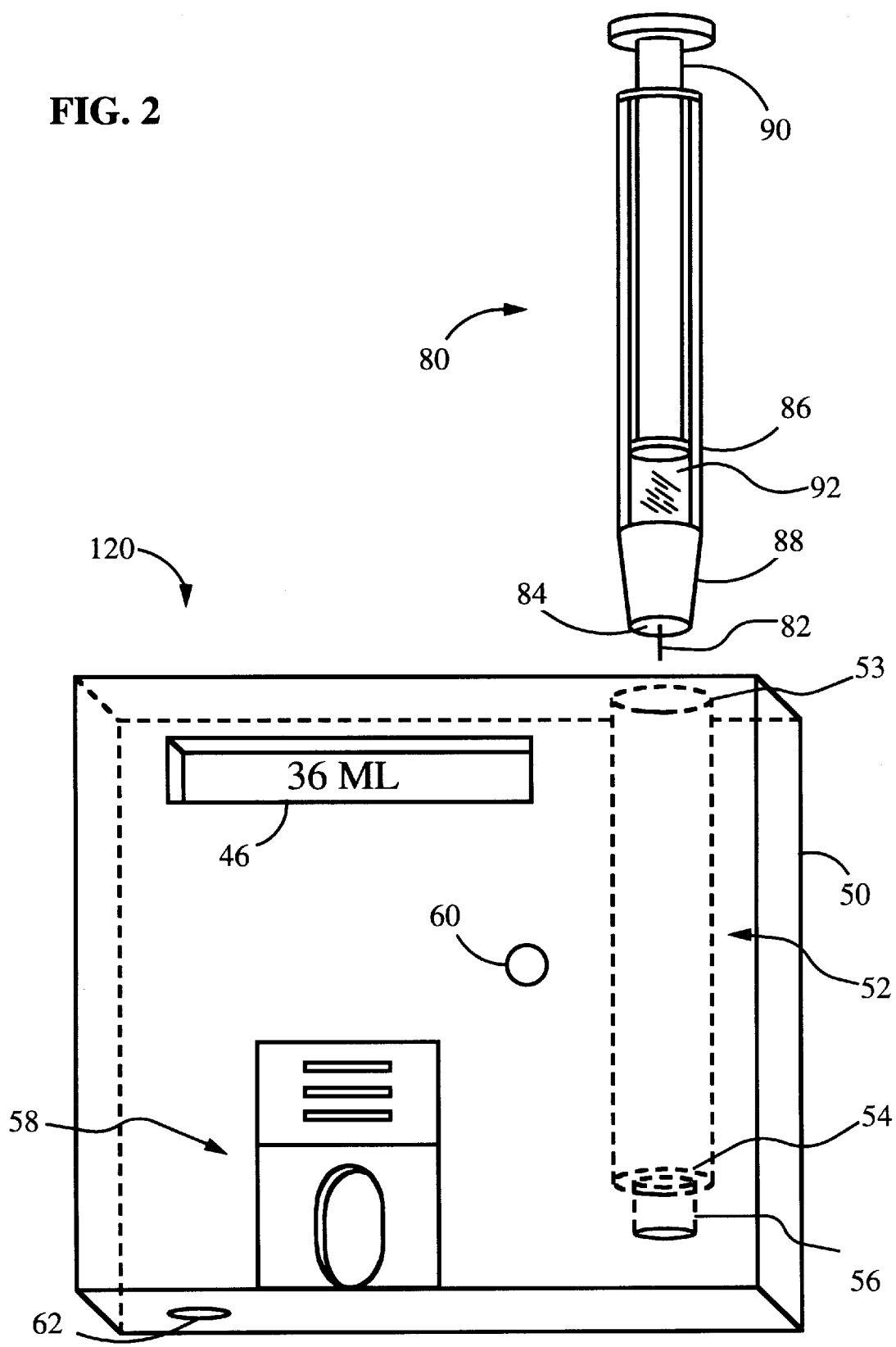
FIG. 2 shows a perspective view of a preferred apparatus of the present invention.

FIG. 2 shows a perspective view of an apparatus 120, according to a preferred embodiment of the present invention. Apparatus 120 comprises a housing 50 enclosing the various electronic components of apparatus 120. Housing 50 preferably comprises a metal layer for shielding internal components of apparatus 120 from external electric fields, and in particular the capacitive components of apparatus 120 (see below). As is apparent to the skilled artisan, care should also be taken to minimize all stray capacitances. Housing 50 is sufficiently compact to allow apparatus 120 to be hand-held and carried by a user. Apparatus 120 has dimensions on the order of centimeters (<20 cm), and a weight not exceeding hundreds of grams.

Display 46 is recessed within housing 50. A patient interface 58 of testing device 44 is also coupled to housing 50. The patient places his or her finger on patient interface 58, allowing testing device 44 to perform a blood glucose measurement for the patient. Blood glucose meters are well known in the art and will not be discussed here in detail. A dose measurement control 60 of control means 34 is coupled to housing 50, and allows the patient to specify when dose measurements are to be performed by apparatus 120 (see below). A port 62 allows data transfer between recording device 40 and patient computer 24.

Housing 50 also encloses a holder 52 for receiving and snugly holding a syringe 80 in the measurement position. A circular opening 53 within housing 50 provides access to holder 52. Holder 52 has a well-like shape for laterally enclosing syringe 80. Holder 52 defines an enclosed space 56 opposite opening 53, for accommodating a needle 82 of syringe 80 when syringe 80 is in the measurement position. Syringe 80 is preferably a conventional plastic syringe. Syringe 80 comprises a barrel 86 and a plunger 90, defining a space for a liquid 92. Liquid 92 is preferably insulin. Plunger 90 is capable of longitudinal motion relative to barrel 86, for adjusting the volume available to liquid 92. Holder 52 comprises an alignment ledge 54 for aligning a barrel 86 of to holder 52 in the measurement position. A contact surface 84 of syringe 80 is in contact with alignment ledge 54 when syringe 80 is in the measurement position.

FIG. 3-A shows a longitudinal sectional view through syringe 80 and holder 52, with syringe 80 in the measurement position. FIG. 3-B shows a transverse sectional view of the arrangement of FIG. 3-A. A capacitive element 100 consists of a single capacitor defined between an electrode 100a and liquid 92. Electrode 100a is a cylindrical copper sheet embedded in a plastic side wall of holder 52, and electrically connected to measuring device 32. Electrode 100a encloses syringe 80 externally and laterally. Liquid 92 is connected to measuring device 32 through needle 82 and a needle contact 83 coupled to holder 52. Needle contact 83 is a corrosion-resistant metal block having a sloped (conical) side wall 85 for contacting needle 82 when syringe 80 is in the measurement position.

The dielectric constant within capacitive element 100 is relatively spatially invariant and does not change substantially with the quantity of liquid 92. The dielectric constant within capacitive element 100 is determined by the materials and/or thicknesses of barrel 86, the air between barrel 86 and the side wall of holder 52, and the portion of the side wall of holder 52 between electrode 100a and barrel 86. Neglecting edge effects and effects stemming from the non-ideal conductivity of liquid 92, the capacitance of capacitive element 100 is then primarily determined by its surface area, which is proportional to the longitudinal extent x of liquid enclosed by electrode 100a.

To operate apparatus 120, a patient inserts the manufacturer-provided syringe 80 in holder 52 prior to administration of the dose. When syringe 80 is pressed against alignment ledge 54 and needle 82 contacts needle contact 83, syringe 80 is in the measurement position. The patient presses button 60 to activate measuring device 32. Measuring device performs a measurement of the capacitance of capacitor 100. Computing device 36 then determines the liquid quantity within syringe 80. Recording device 40 records the liquid quantity as the administered dose, in conjunction with the current date and time obtained from clock 48. Recording device 40 may also record condition data received from testing means 44, and the associated date and time. Recording device 40 then contains the patient's blood glucose and insulin dose histories. The patient periodically (e.g. weekly) connects his or her apparatus 120 to patient computer 24 and downloads the histories stored in recording device 40. The histories are then periodically transmitted to clinician's computer 26.

FIG. 4-A shows a longitudinal sectional view of an alternative capacitive element geometry of the present invention, while FIG. 4-B shows a transverse sectional view of the geometry of FIG. 4-A. A capacitive element 200 is coupled to holder 52, and is situated completely externally to syringe 80. Capacitive element 200 comprises a plurality of independent, longitudinally spaced, stacked capacitors 200a–e. Each capacitor 200a–e is independently connected to measuring device 32, and measuring device 32 determines the capacitive response of each capacitive element independently. A capacitive response pattern of capacitive element 200 (the ensemble of capacitive responses of capacitors 200a–e) is indicative of the quantity of liquid 92 within syringe 80. The use of plural stacked capacitors reduces the vulnerability of a system of the present invention to dosage determination errors caused by a constant capacitance offset.

Capacitor 200a comprises electrodes 200a',a" embedded within the side wall of holder 52 on opposite sides of syringe 80. Capacitors 200b–e are similar to capacitor 200a and are stacked above capacitor 200a. The surface area of each capacitor 200a–e is constant, and does not depend on the quantity of liquid 92. The effective dielectric constant of each capacitor 200a–e may depend, however, on the quantity of liquid 92. If liquid 92 is substantially conductive, it behaves like an electrode inserted between electrodes 200a' and 200a", thus creating two capacitors in series: one defined by electrode 200a' and liquid 92, the other defined by liquid 92 and electrode 200a". Preferably, the dielectric properties of barrel 86, plunger 90 and liquid 92 are such that the capacitance response pattern of capacitive element 200 is indicative of the position of plunger 90 relative to capacitive element 100 and/or of the quantity of liquid 92 within syringe 80.

FIG. 5-A shows a perspective view of an alternative apparatus 420 of the present invention, suitable for measuring doses using capacitors situated within syringes. A circular placement field 470 is delineated on the outside of a housing 450 of apparatus 420. Placement field 470 is bordered on four sides by rigid positioning studs 472 forming a holder. Placement field 470 includes a circular input contact 474 positioned at the center of field 470 and a ring-shaped output contact 476 positioned concentrically to input contact 474. Input contact 474 and output contact 476 are made of an electrically conductive material, preferably copper, and are connected to measuring device 32.

FIG. 5-B shows a longitudinal sectional view of a syringe 480 suitable for use with the apparatus of FIG. 5-A. Syringe 480 comprises a plunger 490 positioned within a barrel 486. Plunger 490 comprises a cylindrical cap 478 sized so as to fit on placement field 470 between studs 472 when syringe 480 is in a measurement position. Cap 478 comprises an input terminal 412 and an output terminal 414 situated such that input terminal 412 and output terminal 414 are in electrical communication respectively with input contact 474 and output contact 476 when syringe 480 is in the measurement position.

A metallic contact line 401 within plunger 490 establishes electrical communication between output terminal 414 and a cylindrical electrode 400a' situated embedded within the plastic body of plunger 490, along the outside surface of plunger 490. A second cylindrical electrode 400a" is encapsulated in the plastic body of barrel 486, and is co-axial with electrode 400a'. Electrode 400a" is in electrical communication with input terminal 412 through metallic contact lines 402 and 404. Line 402 is situated on the lateral (outside) surface of plunger 490, while line 404 is situated within barrel 486. A sliding electrical contact schematically illustrated as 403 is established between a fixed exposed point of line 404 and various points of line 402 as plunger 490 is moved within barrel 486.

The following discussion is intended to illustrate the invention, and should not be construed to limit the invention. Consider the geometry of FIGS. 3-A and 3-B, for a typical syringe. Neglecting edge effects, the capacitance of capacitive element 100 is approximately $$C \approx 2\pi\varepsilon_{bar} \times \ln\left(\frac{b}{a}\right) \quad [1]$$

where x is the length capacitor 100, a and b are the radii of the cylinders defined respectively by liquid 92 and electrode 100a, and $\varepsilon_{bar}$ is the effective dielectric constant between liquid 92 and electrode 100a. From eq. [1] it can be seen that dC/dx, the variation of the capacitance of capacitor 100 with displacement x, can be maximized for given radii a and b by increasing $\varepsilon_{bar}$. Thus, materials with high dielectric constants are preferred for the space between liquid 92 and electrode 100a.

It will be clear to one skilled in the art that the above embodiments may be altered in many ways without departing from the scope of the invention. Generally, the dose data may include, for example, quantities of liquid in the syringe before and/or after the administration of the dose, or capacitive response values before and/or after the administration of the dose; the patient's and/or the clinician's computers then determine the dose administered to the patient from the dose data stored in the recording device. In such an embodiment, calibration data may be stored on the patient's or clinician's computer, and the apparatus may lack a computing device. The patient computer need not be a conventional personal computer, but can be in general any data storage device or device allowing communication between the patient's measurement apparatus and the clinician's data storage device or server. An apparatus of the present invention may connect directly to a clinician's server, rather than indirectly through a patient computer. Various computation and storage devices used in the present invention may generally be implemented through software or dedicated hardware, or combinations thereof. For a multiple-delivery injection device such as an injection pen, liquid quantities before and after each injection are measured and the administered dose is taken to be the difference between the two quantities. The present invention is not limited to diabetes care, and may be used for monitoring patient compliance with any injection-based treatment program.

Various capacitor geometries and placements may be suitable in a device of the present invention. In particular, the capacitor need not laterally enclose the syringe completely or even partially, as long as the capacitive element is capacitively coupled to the syringe. The method does not require the presence of a plunger to determine capacitance. A method of the present invention may be used to capacitively measure liquid levels in plungerless syringes operated using air pressure, for example.

Accordingly, the scope of the invention should be determined by the following claims and their legal equivalents.

What is claimed is:

1. An apparatus for capacitively measuring and electronically recording a dose from a syringe, comprising:
    a) a holder for receiving and holding said syringe in a measurement position;
    b) at least one capacitor electrode positioned on said holder such that a capacitive response generated through said electrode is indicative of said dose when said syringe is in said measurement position;
    c) a measuring device in communication with said capacitive element, for measuring said capacitive response; and
    d) a recording device in communication with said measuring device, for recording a dose datum indicative of said capacitive response, whereby said dose datum is indicative of said dose.

2. The apparatus of claim 1 wherein:
    a) said holder comprises a well laterally enclosing said syringe in said measurement position; and
    b) said capacitive element is coupled to said well so as to externally and laterally enclose said syringe in said measurement position.

3. The apparatus of claim 1 wherein said capacitive response is generated by a liquid held by said syringe and said at least one capacitor electrode positioned on said holder.

4. The apparatus of claim 3 wherein said capacitive response is generated by a syringe needle in contact with said holder, for establishing an electrical communication between said measuring device and said syringe needle when said syringe is in said measurement position, wherein said syringe needle is electrically connected through said liquid.

5. The apparatus of claim 1 wherein said capacitive element comprises:
    a) a first electrically conducting longitudinal plate coupled to said holder; and
    b) a second electrically conducting longitudinal plate coupled to said holder opposite said first longitudinal plate, and electrically insulated from said first plate.

6. The apparatus of claim 1 wherein said capacitive element comprises a plurality of longitudinally-spaced capacitors such that said capacitive response comprises a capacitive response pattern of said plurality of capacitors.

7. The apparatus of claim 1 further comprising a port in communication with said recording device, for transmitting said dose datum from said recording device to a host computer.

8. The apparatus of claim 1 further comprising a testing device for testing a physical condition of a patient and for generating a condition datum representative of said physical condition, said testing device being in communication with said recording device such that said recording device records said condition datum.

9. The apparatus of claim 8 wherein said testing device comprises a blood glucose meter and said condition datum comprises a blood glucose level.

10. The apparatus of claim 1 further comprising a display connected to said measuring device, for displaying said dose.

11. The apparatus of claim 1 wherein said recording device comprises a digital memory unit.

12. The apparatus of claim 1 further comprising a computing device in communication with said recording device, for computing said dose datum from said capacitive response.

13. The apparatus of claim 12 further comprising a calibration memory in communication with said computing device, for providing said computing device with calibration data indicative of a correspondence between said capacitive response and said dose datum.

14. The apparatus of claim 1 further comprising a housing enclosing said measuring device and said recording device, wherein said holder is mechanically coupled to said housing.

15. The apparatus of claim 14 wherein said housing encloses said holder and said capacitive element, for shielding said capacitive element and said syringe from external electric fields.

16. The apparatus of claim 14 wherein said housing is sufficiently compact to be hand-held and carried by a patient.

17. The apparatus of claim 1 wherein said dose comprises an insulin dose.

18. A diabetes monitoring and insulin recording apparatus for recording an insulin dose from a syringe, said apparatus comprising:
    a) a holder for receiving and holding said syringe containing insulin in a measurement position;
    b) a capacitive element positioned on said holder such that a capacitive response of said capacitive element is indicative of said insulin dose when said syringe is in said measurement position;
    c) a measuring device in communication with said capacitive element, for measuring said capacitive response;
    d) a computing device in communication with said measuring device, for computing from said capacitive response a dose datum indicative of said insulin dose;
    e) a blood glucose meter for determining a blood glucose datum indicative of a blood glucose level; and
    f) a recording device in communication with said computing device and said blood glucose meter, for recording said dose datum and said blood glucose datum.

19. The apparatus of claim 18 further comprising a port connected to said recording device, for transmitting said dose datum and said blood glucose datum from said recording device to a host computer.

20. The apparatus of claim 19 further comprising a display connected to said measuring device, for displaying said insulin dose and said blood glucose level.

21. An apparatus for capacitively measuring and electronically recording a dose, said apparatus comprising:
    a) a syringe comprising an input terminal, and output terminal and a capacitive element for generating a capacitive response indicative said dose;
    b) a housing enclosing a measuring device and a recording device; and c) a field coupled to said housing, comprising:
   an input contact for contacting said input terminal of said syringe when said syringe is in a measurement position, and
   an output contact for contacting said output terminal of said syringe when said syringe is in said measurement position; wherein
said input terminal and said output terminal are connected to said capacitive element,
said input contact and said output contact are connected to said measuring device such that said measurement device is capable of measuring said capacitive response when said input terminal contacts said input contact and said output terminal contacts said output contact, and
said recording device is connected to said measuring device, for recording a dose datum indicative of said capacitive response, whereby said dose datum is indicative of said dose.

22. A method of calibrating an apparatus for capacitively measuring and electronically recording a dose delivered using a syringe, comprising the steps of:
   a) placing a syringe in a holder;
   b) measuring a plurality of capacitive responses of a capacitive element mechanically coupled to said holder and capacitively coupled to said syringe, wherein each of said plurality of capacitive responses is indicative of a distinct predetermined liquid quantity in said syringe, and said plurality of capacitive responses correspond to a range of potential liquid quantities in said syringe; and
   c) recording calibration data indicative of said plurality of capacitive responses, whereby said calibration data establishes a correspondence between said plurality of capacitive responses and liquid quantities within said range of potential liquid quantities in said syringe.

23. An apparatus for capacitively measuring and electronically recording a dose, comprising:
   a) a syringe with a compartment for holding a volume of medication and a first capacitor electrode capable of establishing contact with said volume of medication;
   b) a holder with a second capacitor electrode on said holder, said holder for receiving and holding said syringe in a measurement position wherein said first capacitor electrode, said second capacitor electrode and said volume of medication generate a capacitive response indicative said dose;
   c) a measuring device in communication first capacitor electrode and second capacitor electrode for generated a measurement of said capacitive response; and
   d) a recording device in communication with said measuring device, for recording a dose datum indicative of said measurement of said capacitive response, whereby said dose datum is indicative of said dose.

24. The apparatus of claim 23 said first capacitor electrode is a conductive syringe needle.

* * * * *